United States Patent [19]  [11] 4,187,253
Kurtz  [45] Feb. 5, 1980

[54] PROCESS AND APPARATUS FOR ISOTHERMAL CHLORINATION OF HYDROCARBONS

[75] Inventor: Bruce E. Kurtz, Marcellus, N.Y.

[73] Assignee: Allied Chemical Corporation, Morristown, N.J.

[21] Appl. No.: 644,788

[22] Filed: Dec. 29, 1975

Related U.S. Application Data

[60] Continuation-in-part of Ser. No. 363,445, May 24, 1973, abandoned, which is a division of Ser. No. 167,733, Jul. 30, 1971, abandoned.

[51] Int. Cl.² ............................................. C07C 17/02
[52] U.S. Cl. ........................... 260/662 R; 260/654 H; 260/658 R; 260/656 R
[58] Field of Search ........... 260/654 H, 656 R, 658 R, 260/662 R

[56] References Cited

U.S. PATENT DOCUMENTS

| | | | |
|---|---|---|---|
| 1,333,328 | 3/1920 | Martin | 23/285 |
| 2,440,768 | 5/1948 | Churchill | 260/654 H |
| 2,585,469 | 2/1952 | Johnson | 260/662 R |
| 2,676,998 | 4/1954 | Kuntz et al. | 260/654 H |
| 3,138,643 | 6/1964 | Taylor et al. | 260/658 R |
| 3,256,802 | 6/1966 | Karr | 261/122 UX |
| 3,482,947 | 12/1969 | Jacobsen et al. | 23/285 |
| 3,677,714 | 7/1972 | Ledgett | 23/285 |

Primary Examiner—Delbert E. Gantz
Assistant Examiner—Joseph A. Boska
Attorney, Agent, or Firm—Micahel S. Jarosz

[57] ABSTRACT

Process is provided for isothermal chlorination of certain hydrocarbons wherein a gas containing the selected hydrocarbon is passed to a first elongated reaction zone, and a gas containing chlorine is passed into a second elongated gas zone positioned along said first zone, said first and second zones being separated by a porous member. The pressure of gases within the second zone is maintained in excess of the pressure in the first zone for diffusion of chlorine through the porous member into the first zone, which is maintained under conditions sufficient to effect reaction therein of at least a portion of diffused chlorine with the hydrocarbon for production of the desired chlorinated hydrocarbon. The reaction product containing the desired chlorinated hydrocarbon is discharged from the first zone.

7 Claims, 10 Drawing Figures

PRODUCT COMPOSITION FOR METHANE CHLORINATION IN A TUBULAR FLOW REACTOR ($K_5 = K_6 = K_7 = 1$)

FIG. 6

$c_m$ = CONCENTRATION OF COMPONENT $AX_{4-n}Y_n$ IN THE BULK PHASE.

$c'_m$ = CONCENTRATION OF COMPONENT $AX_{4-n}Y_n$ IN THE REACTION FILM.

FIG. 8

PRODUCT COMPOSITION FOR CONSECUTIVE-COMPETITIVE REACTIONS IN A POROUS TUBE REACTOR IN MODERATELY-DEVELOPED LAMINAR FLOW (R = 9)

PROCESS AND APPARATUS FOR ISOTHERMAL CHLORINATION OF HYDROCARBONS

CROSS-REFERENCE TO RELATED APPLICATION

This application is a continuation-in-part of co-pending application U.S. Ser. No. 363,445, filed May 24, 1973, now abandoned, which is a divisional application of U.S. Ser. No. 167,733, filed July 30, 1971, now abandoned.

BACKGROUND OF THE INVENTION

1. FIELD OF THE INVENTION

This invention relates to process and apparatus for chlorination of a gaseous hydrocarbon of one to two carbon atoms and their partially chlorinated derivatives. More specifically it relates to chlorination of such hydrocarbons in a reactor employing a porous member to produce various commercially desirable chlorinated derivatives, economically and in high yield.

2. DESCRIPTION OF THE PRIOR ART

Chlorinated derivatives of one and two carbon hydrocarbons are widely employed in the industry in a variety of applications, including such uses as solvents and intermediates in the production of refrigerants and other chemicals. However, production of these chlorinated derivatives from one and two carbon hydrocarbons, their partially chlorinated derivatives and mixtures thereof by first order, consecutive-competitive reactions with chlorine is complicated by the formation of undesired by-products, e.g. partially chlorinated intermediates. When tubular flow and back-mix reactors are employed in the chlorination of methane and partially-chlorinated derivatives thereof, relatively high amounts of undesired partially-chlorinated by-products have been found to be produced at the expense of the desired carbon tetrachloride. In the chlorination of ethane and partially-chlorinated ethanes, relatively high amounts of undesired chloroethanes have been found to be produced at the expense of the desired chloroethylenes. Moreover, since the chlorination reactions are exothermic, conventional reactors are disadvantaged by the practical limits placed on the rate of chlorine fed to the reactor due to difficulty in removing the heat of reaction and, hence, in controlling the reaction temperature. Excessively high temperatures are not desired because they result in formation of large amounts of carbon, due to pyrolysis of the hydrocarbon feed, which fouls the reactor and downstream equipment. Thus, the prior art has typically employed staged reactions (to provide incremental reaction of the hydrocarbon and chlorine), with intermediate cooling or with extensive recycle of less highly chlorinated by-products in order to obtain the desired chlorinated hydrocarbon. Use of staged reaction methods or of extensive recycles is undesirable because of the large amount of equipment required and the consequent high cost.

SUMMARY OF THE INVENTION

According to the present invention, a process is provided for isothermal chlorination of a feed stream selected from the group consisting of hydrocarbons having from 1 to 2 carbon atoms, their partially chlorinated derivatives and mixtures thereof, to form chlorinated derivative thereof, which comprises (a) passing a gas containing the feed stream under pressure into a first elongated gas zone, (b) passing a gas containing chlorine under pressure into a second elongated gas zone positioned along said first gas zone, said first and second elongated gas zones being separated by a porous member, (c) maintaining the pressure of the gases in said second gas zone in excess of the pressure in said first gas zone, (d) maintaining said first gas zone under conditions sufficient to effect reaction therein of at least a portion of said diffused chlorine with the feed stream for production of the desired chlorinated derivatives, and (e) withdrawing the gas product containing the desired chlorinated derivatives from said first gas zone.

The process of the present invention provides reaction between the chlorine and the feed stream in the first gas zone as the feed stream flows longitudinally therethrough, while the gas containing chlorine diffuses thereto through the porous member which separates the two gas zones. The first gas zone may be equipped with cooling means so as to remove the heat generated by the reaction of chlorine and the feed stream.

The present invention has been found to allow use of increased chlorine-to-feed stream ratios to provide substantially complete conversion of the feed stream in the reactor, thereby eliminating the need for staged reactions with intermediate cooling or extensive recycle of less highly chlorinated by-products or unreacted gases. Moreover, the present invention has been found to markedly reduce the formation of by-products at a given chlorine-to-feed stream ratio and temperature, thereby reducing or eliminating the need to separate less highly chlorinated by-products from the product stream. Further, the desired reactions have been found to proceed at lower temperatures, thus providing concomitant savings in heat requirements and in increased equipment life.

With respect to the chlorination of methane, substantially complete suppression of intermediate products has been found to result from operation of a preferred embodiment of the process of the present invention wherein the flow of the gas through the first elongated gas zone is maintained in the laminar region.

In prior art methods, chlorine and hydrocarbon reactants are conventionally introduced to a tubular flow or back-mixed reactor at the same point, so that the rate of chlorination reaction is initially at a maximum, decreasing as the amount of free chlorine is depleted in the reaction chamber. If the reaction is strongly exothermic (as is generally the case for these chlorination reactions) the rate of heat evolution is initially very large. In the case of a tubular flow reactor surrounded by a cooling medium, the temperature will rapidly rise to a maximum near the feed end of the reactor and gradually decrease towards the exit end as the chlorine reactant is exhausted. Thus, while chlorine to methane molar feed ratios approaching 4.0 would provide a gas containing close to 100 mole percent carbon tetrachloride, this temperature rise imposes a practical upper limit on the molar ratio of chlorine to hydrocarbon in the feed, typically about 0.25, so that staged introduction of chlorine and intermediate cooling are required, an expensive and wasteful use of alternate heating and cooling means. In contrast, in the process of the present invention, the reaction rate is substantially uniform along the length of the elongated reaction zone, providing a uniform rate of heat evolution and, with the provision of suitable cooling means, allowing obtainment of essentially isothermal conditions in the reaction zone, removing the need to employ staged chlorine addition and interstage cooling.

The method of chlorination of the present invention has additional advantages over conventional methods. Exceptionally high yields are obtained per pass, and the uniform rates of heat evolution and use of suitable cooling means leads to essentially isothermal operation, thus preventing pyrolysis of the feed stream, so that, consequently, virtually no carbon is formed to foul the reactor and downstream equipment.

Apparatus for carrying out the process of the present invention are also provided and comprise an elongated housing provided with first and second elongated gas passages disposed therein, said first passage positioned substantially along said second passage and being separated therefrom by a porous member; means for introducing a first reactant gas into the first elongated gas passage; means for introducing a second reactant gas into the second elongated gas passage; means for maintaining the pressure in said second gas passage in excess of that within said first gas passage for substantially uniform diffusion of said second reactant gas from the second gas passage through the porous member to the first gas passage; means for maintaining the first gas passage under conditions sufficient to effect reaction therein of diffused second reactant gas with first reactant gas; and outlet means for discharging the reaction mixture from said first gas passage. Heat exchange means for controlling the temperature within said first gas passage for reaction of said first and second reactant gases may also be provided.

BRIEF DESCRIPTION OF THE DRAWINGS

Preferred embodiments of the apparatus of the present invention are illustrated in the accompanying drawings wherein.

The particulars of the method of constructing the apparatus of the present invention which are not specified herein are considered to be within the knowledge of a reasonably skilled workman in the art.

DETAILED DESCRIPTION OF THE INVENTION

The apparatus of the present invention for chlorination of 1 and 2 carbon hydrocarbons, their partially chlorinated derivatives and mixtures thereof, comprises, in its broadest sense, an elongated housing provided with first and second elongated gas passages disposed therein. These passages are positioned substantially along one another and are separated by a porous member, for the major portion of their length, so that the desired gases may pass from the second passage into the first passage along the major portion of the length of these elongated gas passages. The shape of the cross-section of the elongated first and second gas passages is not critical, and thus, these passages may be rectangular, circular or assymmetrical. However, it is preferred that first and second gas passages be cylindrical, and hence of a circular cross-section.

In the preferred embodiment, the apparatus of the present invention for chlorination of 1 and 2 carbon hydrocarbons, their partially chlorinated derivatives and mixtures thereof, comprises an elongated porous tube having an elongated gas zone disposed therein, and provided with gas inlet means for passing gas into said elongated gas zone; an outer elongated tube provided with substantially gas-impervious outer walls surrounding the porous tube and adapted to define an elongated annular gas zone internal to the outer tube and external to the porous member; means for introducing gas into the annular gas zone at a rate such that the flow of gas through said first gas passage is in the laminar region; means for maintaining the pressure in the elongated gas zone internal to the porous tube in excess of the pressure in the annular gas zone for diffusion of gas from the elongated gas zone into the annular gas zone, and outlet means for discharging gas from the annular gas zone. Heat exchange means for controlling the temperature within the annular gas zone may also be provided.

Most preferably, the elongated porous tube is open at one end and closed at the other. Thus, the preferred embodiment of the process of the present invention comprises passing a chlorine-containing gas under pressure into an elongated inner zone provided in an elongated porous tube closed at one end and open at the other end; passing a gas containing the feed stream of hydrocarbons having from 1 to 2 carbon atoms, their partially chlorinated derivatives and mixtures thereof, through an elongated annular reaction zone surrounding the porous tube; maintaining the pressure in said inner zone in excess of the pressure in said annular reaction zone for diffusion of chlorine-containing gas through said porous tube; reacting said diffused chlorine-containing gas with said feedstream in said annular reaction zone; and discharging the reaction product mixture from said reaction zone. In such an embodiment, the present invention would provide reaction between the chlorine and the feed stream in the annular space surrounding the porous axial core as the hydrocarbon reactant flows longitudinally through the annular reaction zone while the chlorine reactant diffuses radially from a porous axial core.

The chlorination apparatus of the present invention herein referred to as a porous tube reactor may be used as a single unit. Alternatively, one or more serially arranged units, or a plurality of unit reactors arranged for parallel operation, may be employed. In the preferred embodiment, a single unit of the porous tube reactor of the present invention comprises two concentric tubes with the inner tube being preferably closed at one end and being provided with a porous wall and an inlet for introducing a reactant gas therein. The outer tube is positioned about the inner tube to provide an annular space longitudinally therebetween and is provided with an inlet for a second reactant gas and an outlet for the gas reaction product. Optionally, heat transfer means can be associated with the outer tube.

In use, a gas mixture containing chlorine, preferably as molecular chlorine, is introduced into the inner tube and is diffused radially, and preferably substantially uniformly, into the annulus defined by the inner and outer tubes, reacting therein with a gas containing the hydrocarbon reactant introduced into the annulus. The reaction product is removed from the annulus through the outlet thereof, which outlet is generally positioned at a point removed from the inlet of the annulus. The reactor of this invention is specifically designed for isothermal reaction temperatures and therefore the design is such that the reaction takes place in the annulus where the temperature control to assure isothermal conditions is possible. In addition to temperature control, the system, of which this reactor is a part, is also designed for careful control of such variables as flow rate, proportion of reactants, residence time, and importantly, the degree of mixing in the annulus.

In the event a plurality of unit reactors is employed, they may be arranged for parallel operation in an outer casing with inlet and outlet ports, so that a heat transfer medium may circulate within the outer shell or jacket around the outer tubes of the plurality of units. Such an apparatus can be fabricated, for example, with a plurality of porous tube reactors spaced longitudinally within a containing casing.

Reference is now made to the accompanying drawings wherein like numerals indicated like or corresponding parts throughout the several views.

Figure 1:
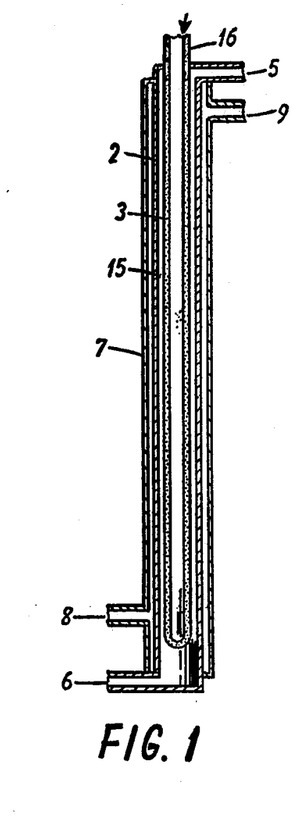
FIG. 1 is a longitudinal half section of one embodiment of the preferred apparatus of the present invention.
Figure 2:
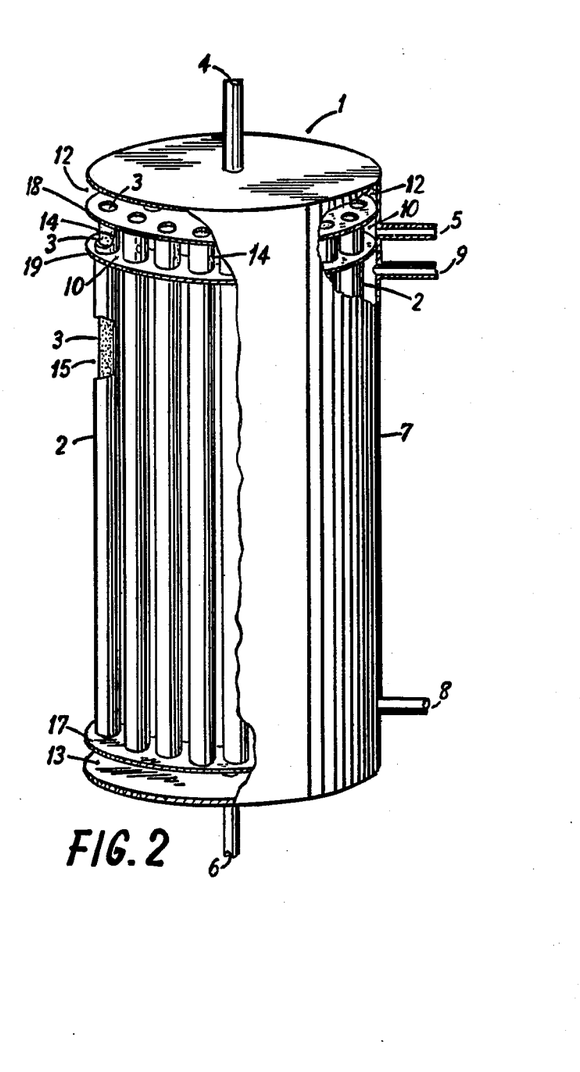
FIG. 2 is a perspective break-away view illustrating a preferred embodiment wherein a plurality of porous tube reaction units are combined for parallel action.

Referring to the porous tube reactor of FIG. 1, a plurality of which are also shown in the assembly of FIG. 2, the individual reactor comprises an outer tube 2, which is substantially gas impervious, an inner porous tube 3, a feed inlet 4 for the gas containing chlorine, an inlet 5 for the feed stream containing the selected hydrocarbon reactant, a product outlet 6, and optionally, a jacket 7 for a heat transfer medium, said jacket having an inlet 8, and an outlet 9 for the heat transfer medium. The unit and the assembly comprising a plurality of these units should be resistant to chlorine and to HCl gas and the organic and chlorinated organic gases which may be formed as by-products or employed as starting materials.

FIG. 2 illustrates a preferred embodiment of the present invention wherein a bundle of porous tube reactor units are arranged in parallel, in this instance in a cylindrical container. There are several ways of this arrangement can be effected. In the method illustrated, there are two tube sheets, 18 and 19, at the upper end of the assembly and one tube sheet 17 at the lower end. These tube sheets are sealed along their periphery to the inner surface of the casing 7 to form two compartments or vestibules, 10 and 12, at the upper end of the assembly and one vestibule 13 at the lower end of the assembly. The outer impervous tubes are sealed into the bottom tube sheet 17 in the usual manner so that they then communicate with vestibule 13. The upper ends of these impervous tubes pass through and are sealed into tube sheet 19. The tubes then terminate at tube sheet 18, being sealed against the lower surface of the latter tube sheet. Since they are sealed to undersurface of tube sheet 18, the tubes do not communicate with vestibule 12 but surround the porous tube 3 which does so communicate. At least one opening, 14, is made in the impervous tube within the distance between tube sheet 18 and 19. With this arrangement, vestibule 12 is then in communication with vestibule 10 when one includes in the route of communication, the pores of the respective porous tubes. The short section of porous tube extending between the sheets 18 and 19 is preferably rendered impervous as is also section 16 of the porous tube of FIGS. 1 and 3, and section 16a of the porous tube of FIG. 3.

Figure 3:
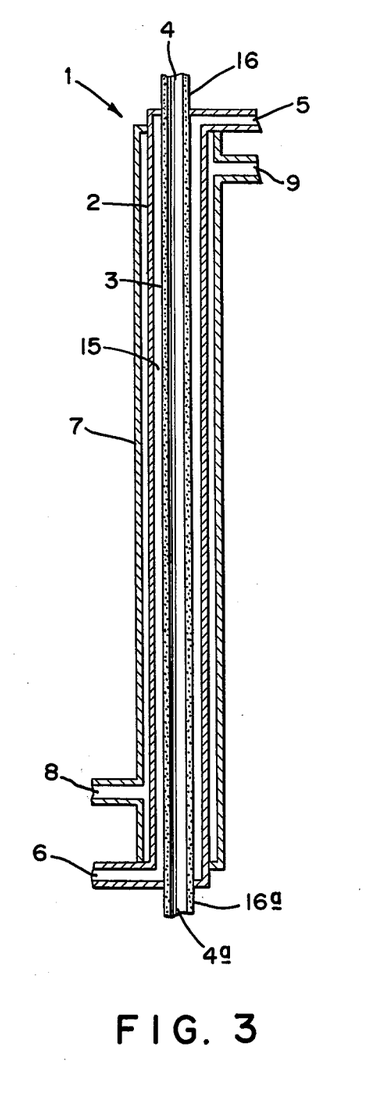
FIG. 3 is a longitudinal half section of a second embodiment of the preferred apparatus of the present invention.

In operation, a heat transfer medium such as molten sodium nitrate is introduced through inlet 8 of FIG. 1, and after circulating around impervous tube 2 exits at outlet 9. In the case of FIG. 2, there are no individual jackets surrounding impervous tubes 2 as in FIG. 1. Such individual jackets are not necessary as the heat transfer medium enters the casing at inlet 8, circulates about all impervous tubes 2 and then exits at outlet 9. With respect to both FIG. 1 and FIG. 2, the gas containing chlorine is introduced at inlet 4 and the hydrocarbon feed stream is introduced at inlet 5. In the embodiment of FIG. 3, the gas containing chlorine is introduced to porous tube 3 at inlet 4 and that portion of this gas which does not pass through the porous walls into reaction zone 15, exits porous tube 3 at outlet 4a. In FIGS. 1 and 3 the gas containing chlorine diffuses substantially uniformly through porous wall 3 to react with the hydrocarbon in annular zone 15 between porous tube 3 and impervous tube 2. Because of the substantially uniform introduction of the gas containing chlorine throughout the full length of the porous tube and the application of a heat transfer medium to the exterior wall of tube 2 to initiate the reaction and to supply or extract heat as required, essentially isothermal reaction conditions in reaction zone 15 can be readily maintained if desired. The reaction product is removed from zone 15 through outlet 6. If desired, a portion of this reaction mixture may be recycled for further chlorination. In the apparatus of FIG. 2, a novel arrangement prevents the premature reaction between a portion of the reactants in vestibule 10. The hydrocarbon feed stream entering vestibule 10 does not enter the impervious tubes at their intersection with tube sheet 19, but rather through perforations 14 in the side of the tubes. To further eliminate any opportunity for a portion of the reaction to occur within vestibule 10, that portion of the porous tube which extends between tube sheets 18 and 19 is rendered impervious.

In connection with the operation of the multi-tube reactor as illustrated in FIG. 2, it should be noted that the preferred construction minimizes the possibility of the chlorine and hydrocarbon feed stream mixing in vestibule 10 and reacting. It will be noted that in the preferred embodiment the length of the porous tube passing between tube sheets 18 and 19 is impervious and that the hydrocarbon feedstream entering the vestibule 10 at inlet 9 only enters the annulus through one or more openings in each tube, shown at 14, thus as the chlorine first diffuses through the tube it enters the heated section of the annulus where it reacts and does not escape into the vestibule.

The porous members separating the first and second gas passages in the apparatus of the present invention may be made of a wide variety of materials of construction. Vycor or quartz are quite satisfactory as materials of construction, although porous members made from alumina are preferred especially for large-scale operation. Thus, for example, porous alumina, ceramic tubes or even a sintered metal tube, where compatible, may be used as porous tube 3 in the apparatus illustrated in FIG. 1. A fritted Pyrex glass tube may also be employed. The purpose of the pores is to produce a substantially uniform diffusion of chlorine into the first gas zone for reaction with the hydrocarbon feed stream, thus enhancing high yields of the desired chlorinated hydrocarbon product. Thus, it is preferred that the porosity of the porous member be substantially uniform along its length. The average pore diameter of the pores in the porous member may vary from greater than about 0.5 up to about 1000 microns, with a range of from about 5 to 300 microns being preferred. While porous members having an average pore size of less than 0.5 microns may be used, the pressures required for diffusion of gasses therethrough make use of such low porosities undesirable.

For simplicity of construction it is preferred that inner zone 4 in porous member 3 be substantially cylindrical and be of a uniform cross-section, although such uniformity in cross-section is not critical. While porous tube 3 is closed at one end and open at the other end in the preferred embodiment, as shown in FIG. 1, this is not critical, and a porous tube may be employed which is open at both ends, provided the gas containing the hydrocarbon passing longitudinally out of inner zone 4 in such an embodiment does not pass into the annular reaction zone. FIG. 3 illustrates such an embodiment, wherein the gas containing chlorine flows through porous tube 4 as indicated with recycle of non-diffused gases exiting outlet 4a. Moreover, in the embodiment of FIG. 3, the hydrocarbon feed stream can be fed to the core elongated zone 4 with the chlorine gas being fed to annular zone 15 at a greater pressure than is maintained in zone 4 for diffusion of chlorine from annular zone 15 into zone 4 for reaction with feedstream therein. In such an embodiment, the roles of annular zone 15 and inner zone 4 are reversed with the latter zone now comprising the reaction zone, from which product is withdrawn at exit 4a. Nondiffused chlorine may thus be withdrawn via line 6 and recycled to annular zone 15 via line 5.

To provide higher conversions to the desired product, it is preferred that the apparatus of the present invention be characterized by a length-to-diameter ratio of at least about 3:1, and more preferably at least 10:1. As used herein, the length-to-diameter ratio is defined as the ratio of (1) the inside length of the first elongated gas zone wherein the chlorination reaction is effected, to (2) the average cross-sectional diameter of the first elongated gas zone. In the instance in which a porous tube reactor is employed, such as illustrated in FIG. 1, the inside length and inside diameter of outer tube 2 is used to compute this ratio.

The one and two carbon hydrocarbons which may be treated in accordance with the process of the present invention are methane, ethane, ethylene and saturated and unsaturated partially chlorinated derivatives thereof, and mixtures of the above. Partially chlorinated derivatives of the foregoing one and two carbon hydrocarbons include methyl chloride, methylene chloride, trichloromethane, the chloroethylenes (mono-, di-, tri- and tetra-chloroethylene), and the partially chlorinated ethanes, e.g. 1-chloroethane, 1,2-dichloroethane, 1,1-dichloroethane, 1,1,2-trichloroethane, 1,1,1-trichloroethane, 1,1,2,2-tetrachloroethane, 1,1,1,2-tetrachloroethane, and pentachloroethane. The precise chlorinated hydrocarbon or mixtures of chlorinated hydrocarbons obtained as product will, of course, depend on the hydrocarbon or mixture of hydrocarbons selected as starting material. Thus, while the present invention is particularly adapted to high yield production of carbon tetrachloride by controlled isothermal chlorination of methane, and production of methylchloroform, trichloroethylene and tetrachloroethylene by the controlled isothermal chlorination of ethane, a wide variety of product mixtures containing other chlorinated hydrocarbons can also be obtained.

To initiate the reaction and to maintain the desired temperature conditions throughout the chlorination, a heat transfer medium, appropriate to the chlorination being carried out, is circulated around the outer tube. In the equipment shown, this heat transfer medium enters inlet 8 and is discharged via outlet 9. By adjusting the temperature of this circulating medium, employing techniques known to the art, the temperature of the chlorination reaction may be maintained within the range of 250° to 500° C., or desirably between 325° to 375° C. A suitable heat transfer medium is molten sodium nitrate or molten lead.

The molar ratio of the chlorine feed to the hydrocarbon feed will vary widely depending on the hydrocarbon fed, the product desired, and other factors. For example, the chlorine:methane molar feed ratio and the chlorine:ethane molar feed ratio will generally range from about 0.5:1 to about 5:1. However, higher or lower ratios can be employed.

The pressures employed in the first and second elongated gas zones (i.e., annular zone 15 and inner zone 4 in the apparatus of FIG. 1) are not critical and may vary widely. Thus, while pressures of from atmospheric to about 20 psig may be selected for ease of operation, pressures outside this range may also be used. However, to ensure diffusion of chlorine gas to zone 15, the pressure within inner zone 4 is maintained in excess of the pressure in annular zone 15. The pressure within the second elongated gas zone (inner zone 4) typically will be generally from about 0.2" to 6" Hg, and more preferably by about 1" to 2" Hg greater than that within the first elongated gas zone (annular zone 15) in order to assure flow of the chlorine containing gas through the porous wall.

While the following theory of operation should not be considered limiting in any way, it is believed that the desired chlorination reaction should be substantially confined to the surface of the porous tube to suppress formation of undesired by-products, e.g. methylene chloride and chloroform in the case of the chlorination of methane to produce carbon tetrachloride. Moreover, in the case of the chlorination of methane to form carbon tetrachloride, it is important for the rate of the competitive, consecutive reactions of the methane and its chlorinated derivatives with chlorine to form carbon tetrachloride to be fast compared to the rate of diffusion of the methane and chlorinated intermediates between the surface of the porous tube and the bulk phase. It is therefore preferred that the flow of gas through the first gas zone, i.e. annular zone 15 in FIG. 1, be maintained laminar when methane is the hydrocarbon feedstream fed to the reactor and carbon tetrachloride is the desired chlorinated hydrocarbon product. Of course, laminar flow may also be advantageously employed with other hydrocarbon feeds, e.g. ethane. As used herein, the term "laminar" is meant to define fluid flow conditions wherein the individual particles of fluid are flowing in an orderly manner in substantially straight lines parallel to the long axis of the first gas zone (i.e. annular zone 15 in FIG. 1), with substantially no bulk mixing. Thus, turbulent flow, in which the individual particles of fluid flow in an erratic manner with complete bulk mixing, is not preferred.

The working of the preferred porous tube reactor embodiment and, in particular, the importance of controlling the degree of turbulence in the first elongated gas zone wherein the chlorination reactions occur, may be more fully appreciated by the following theoretical explanation which is not, however, in any way intended to limit the applicability of this process.

Consider the following consecutive-competitive reactions, $$AX_{4-n}Y_n + YZ \xrightarrow{k_n} AX_{3-n}Y_{n+1} + XZ \quad (I)$$

wherein n is consecutively equal to 0, 1, 2 and 3, $k_n$ is the reaction rate constant for the n reactant, and A, X, Y and Z represent atoms of carbon, hydrogen, chlorine and chlorine, respectively, for methane chlorination. Thus, the variables $X_{4-n}$ and $Y_n$ represent the number of atoms of hydrogen and chlorine, respectively, in the $AX_{4-n}Y_n$ reactant, e.g. $AX_4$ for n=0 or $AXY_4$ for n=3. According to Fuoss (J. Am. Chem. Soc. 65, 2406 (1943)) and to Natta and Mantica (J. Am. Chem. Soc. 74, 3152 (1952)), the relative amounts of the products of consecutive-competitive reactions are dependent solely on the ratios of the reaction rate constants, $k_n$, and on the type of reactor, as will be shown by the following analysis.

Assuming that the rate of reaction of component $AX_{4-n}Y_n$ is directly proportional to its concentration, designated as $C_m$ (wherein m is an integer of from 0 to 4) then the time rate of change of concentration for each component is equal to the rate at which a component is formed minus the rate at which it is reacted. The relative rate of change of concentration is then found by dividing the expressions for $C_1$, $C_2$, $C_3$ and $C_4$ by that for $C_0$, thus eliminating time as a variable and leading to the following expressions:

$$\frac{dC_1}{dC_0} = K_5 \frac{C_1}{C_0} - 1 \quad (IIa)$$

$$\frac{dC_2}{dC_0} = K_6 \frac{C_2}{C_0} - K_5 \frac{C_1}{C_0} \quad (IIb)$$

$$\frac{dC_3}{dC_0} = K_7 \frac{C_3}{C_0} - K_6 \frac{C_2}{C_0} \quad (IIc)$$

$$\frac{dC_4}{dC_0} = - K_7 \frac{C_3}{C_0} \quad (IId)$$

wherein $K_5 = k_1/k_0$, $K_6 = k_2/k_0$ and $K_7 = k_3/k_0$, the ratios of the individual reaction rate constants.

As is evident from the foregoing, $C_0$ corresponds to the concentration of $AX_4$, $C_1$ corresponds to the concentration of $AX_3Y$, $C_2$ to the concentration of $AX_2Y_2$, and $C_3$ to the concentration of $AXY_3$ and $C_4$ to the concentration of $AY_4$.

Figure 4:
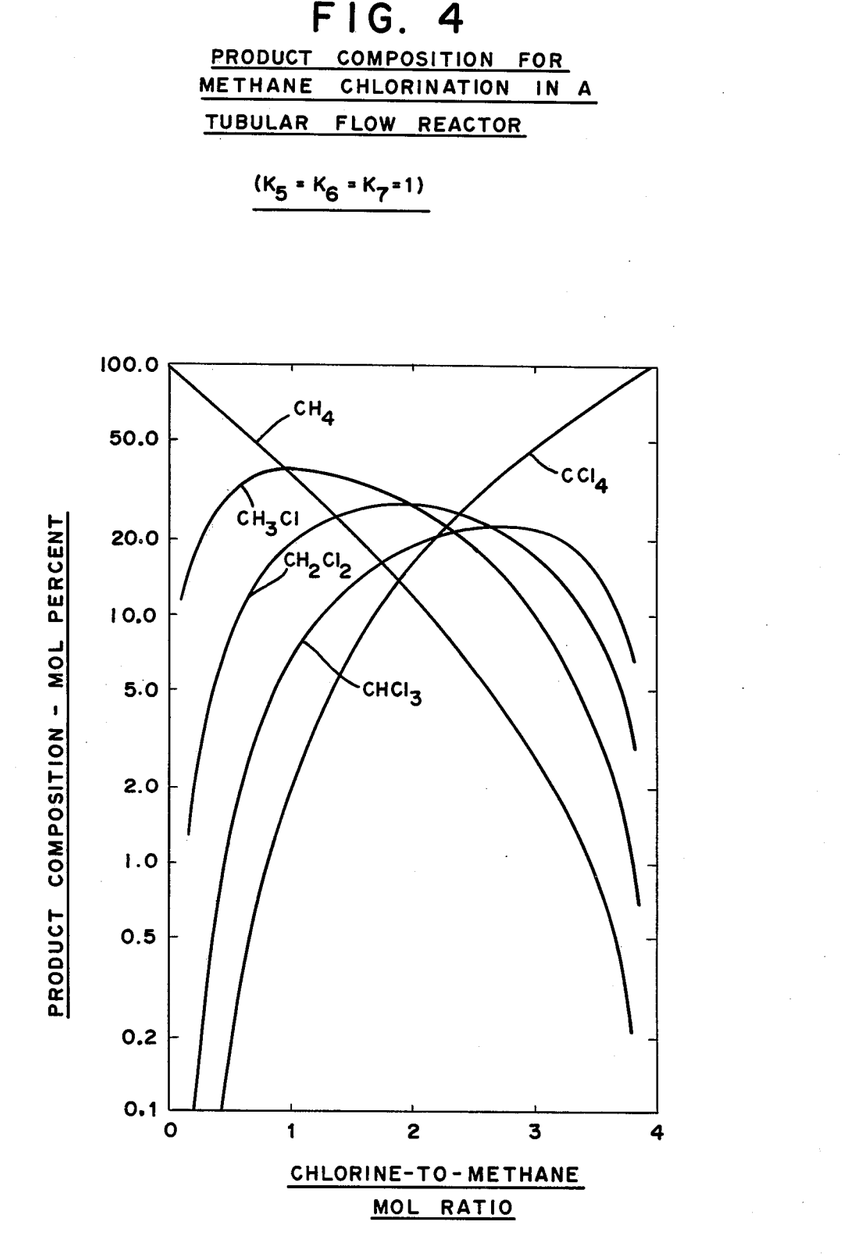
FIG. 4 is a plot of product composition vs. chlorine-to-methane mol ratio for methane chlorination in a tubular flow reactor.

For a tubular flow reactor equations IIa to IId can be integrated either analytically or numerically to give the composition of the reaction products. Product compositions for a feed consisting of pure $AX_4$ and reaction rate constant ratios of unity (i.e., $K_5=K_6=K_7=1$) are calculated from Equations IIa to IId as illustrated in FIG. 4, wherein $CH_4$ is the feed hydrocarbon, $CCl_4$ is the desired chlorinated product and $CHCl_3$, $CH_2Cl_2$ and $CH_3Cl$ are the partially-chlorinated intermediates.

In a back-mixed reactor the concentrations on the right side of equations IIa to IId are constant and equal to those of the exit stream (subscript e) and the derivatives on the left side of equations IIa to IId are replaced by the finite differences between the concentration of the reactor exit stream and the reactor feed stream (subscript f), thus reducing the differential equations to the algebraic expressions IIIa to IIId, which have been arranged to solve for the concentrations of the exit stream.

$$C_{1e} = \frac{C_{0f} - C_{0e} - C_{1f}}{1 + K_5(Q-1)} \quad (IIIa)$$

$$C_{2e} = \frac{K_5(Q-1)C_{1e} + C_{2f}}{1 + K_6(Q-1)} \quad (IIIb)$$

$$C_{3e} = \frac{K_6(Q-1)C_{2e} + C_{3f}}{1 + K_7(Q-1)} \quad (IIIc)$$

$$C_{4e} = K_7(Q-1)C_{3e} + C_{4f} \quad (IIId)$$

wherein $Q = C_{0f}/C_{0e}$.

Figure 5:
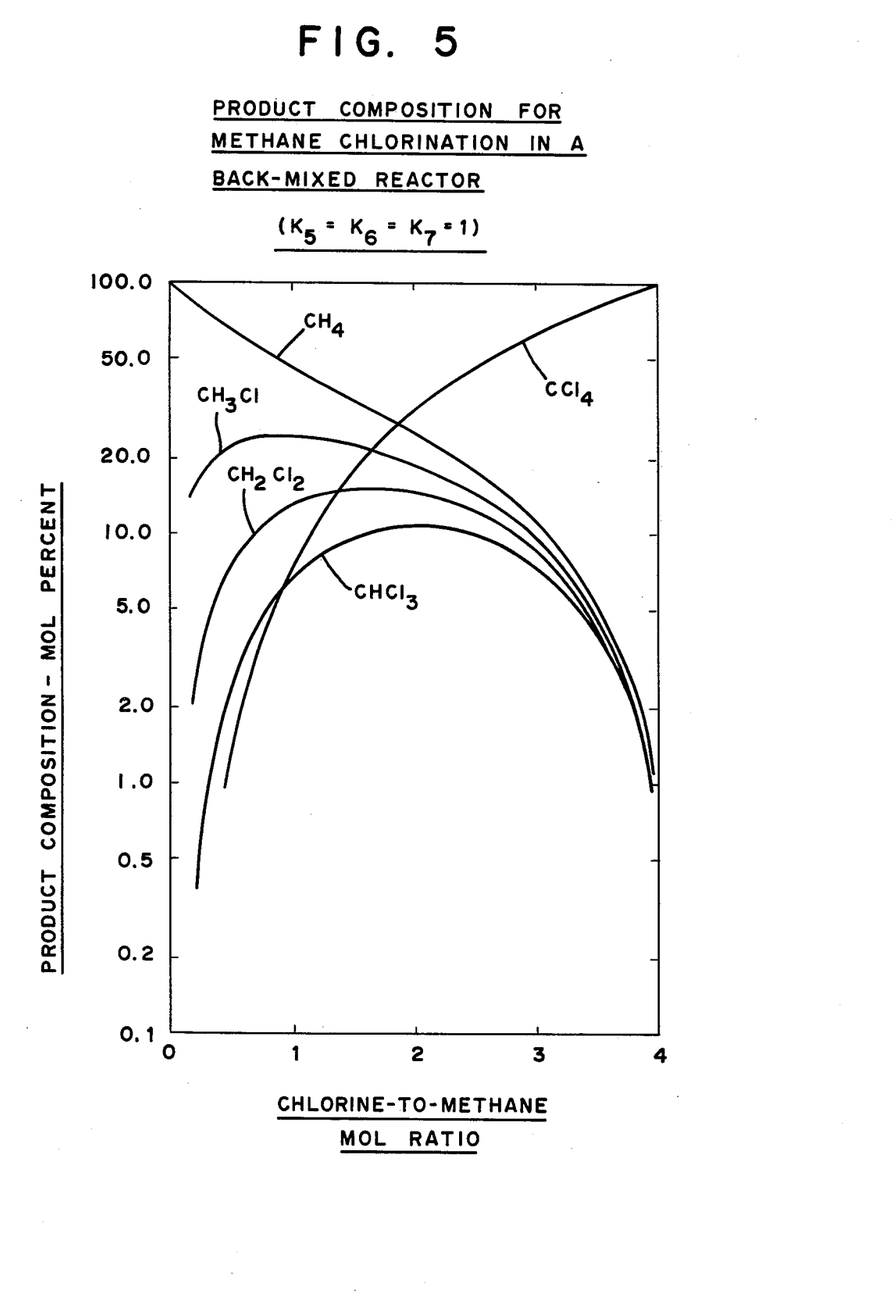
FIG. 5 is a plot of product composition vs. chlorine-to-methane mol ratio for methane chlorination in a back-mixed reactor.

FIG. 5 shows the product compositions for a feed consisting of the pure $AX_4$ and reaction rate constant ratios of unity (i.e., $K_5 K_6 = 7 = 1$) for the case of the back-mixed reactor, as calculated using Equations IIIa to IIId. It will be noted that the concentrations of the intermediate products (i.e., $CHCl_3$, $CH_2Cl_2$ and $CH_3Cl$) are somewhat lower in the back-mixed reactor than in the tubular flow reactor.

To compare the above results using a conventional back-mixed or tubular flow reactor with that obtained using an apparatus of the present invention, reference will be made to the preferred embodiment, the porous tube reactor illustrated in FIG. 1. Referring again to FIG. 1 for purposes of illustration, reactant $AX_4$ is introduced via line 5 into the upper end of annular zone 15 formed by porous tube 3 and outer tube 2. Reactant YZ is introduced into porous tube 3 at inlet 4 and is maintained at a pressure in excess of that in annular zone 15 for diffusion of YZ through porous tube 3 into the zone 15. The feed rate of reactant YZ to porous tube 3 is less than the amount stoichiometrically required for complete conversion of YZ to $AY_4$ (i.e., less than 4 mols of YZ per mole of $AX_4$). The bulk flow in the longitudinal direction of annular zone 15 is laminar. The reaction products are withdrawn from annular zone 15 via line 6.

Figure 6:
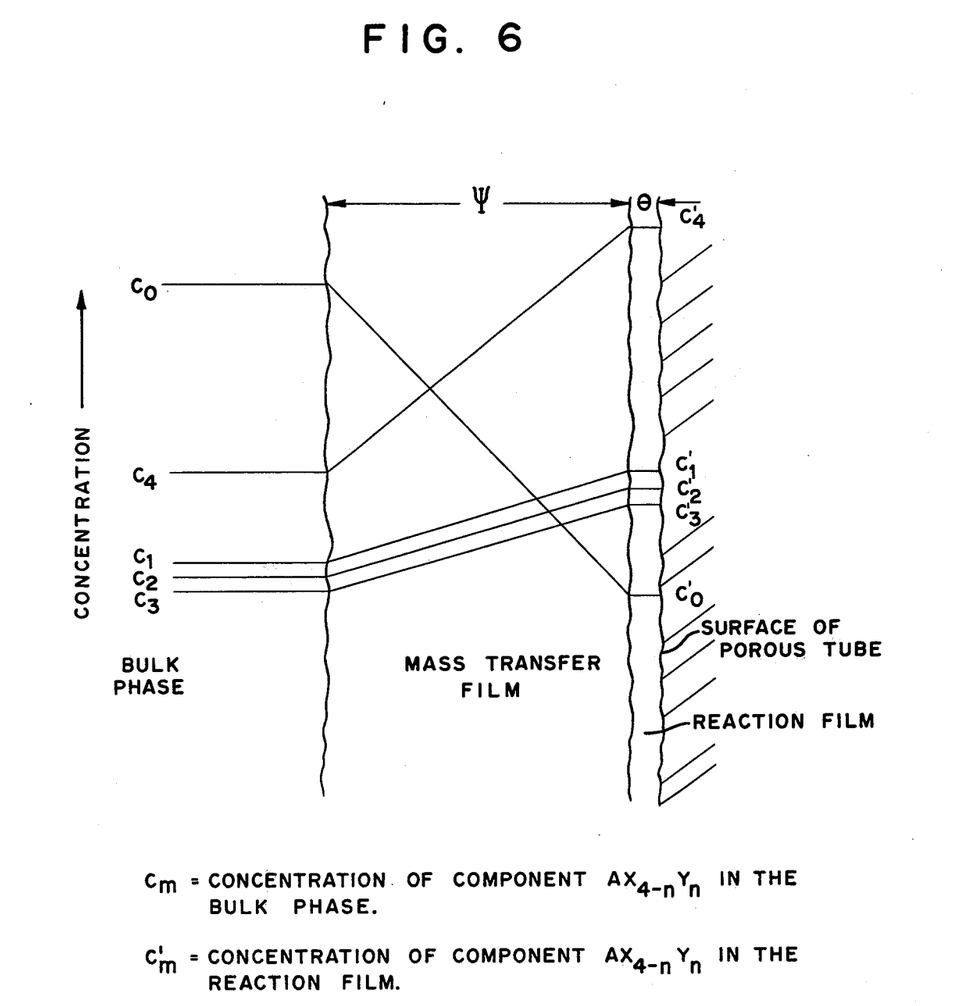
FIG. 6 is a theoretical representation of the bulk phase, mass transfer film and reaction film for laminar flow.

If we assume that the reaction is quite fast, then all the reaction can be regarded as taking place in a very thin film on the surface of the porous tube. This reaction film is assumed to be separated from the bulk phase in the annulus by a mass transfer film. Reactants $AX_{4-n}Y_n$ diffuse from the bulk phase through this mass transfer film to the reaction film while products $AX_{3-n}Y_{n+1}$ diffuse from the reaction film to the bulk phase. This is illustrated by FIG. 6, wherein $C_0$ to $C_4$ are concentrations in the bulk phase, $C_0'$ to $C_4'$ are concentrations in the reaction film, $\theta$ is the thickness of the reaction film and $\Psi$ is the thickness of the mass transfer film.

The composition of the bulk phase will change in the longitudinal direction of flow as the reaction proceeds. It is assumed that the bulk phase constitutes by far the greatest part of the volume of the annulus.

When a molecule of reactant $AX_4$ diffuses to the reaction film on the surface of the porous tube it reacts to form $AX_3Y$. This molecule of $AX_3Y$ can either diffuse back into the bulk phase or it can react further to form, in turn, $AX_2Y_2$, $AXY_3$ and $AY_4$. The last product, $AY_4$, can react no further and hence can only diffuse back to the bulk phase.

The concentrations of the various components in the reaction film on the surface of the porous tube and in the bulk phase depend on the relative rates of diffusion and reaction. If the diffusion rate is fast compared to the reaction rate, then the concentration of the various components will be the same in the reaction film and the bulk phase and the composition of products will be distinguishable from that obtained with a tubular flow reactor. If the reaction rate is fast compared to the diffusion rate then the concentrations in the reaction film and bulk phase will be as shown by FIG. 6.

The equality between the mass flows across the mass transfer film and the reaction rates at the surface of the porous tube leads to the following expressions:

$$\frac{dC_1}{dC_0} = K_5 \frac{C_1'}{C_0'} - 1 = K_1 \frac{C_1 - C_1'}{C_0 - C_0'} \quad \text{(IVa)}$$

$$\frac{dC_2}{dC_0} = K_6 \frac{C_2'}{C_0'} - K_5 \frac{C_1'}{C_0'} = K_2 \frac{C_2 - C_2'}{C_0 - C_0'} \quad \text{(IVb)}$$

$$\frac{dC_3}{dC_0} = K_7 \frac{C_3'}{C_0'} - K_6 \frac{C_2'}{C_0'} = K_3 \frac{C_3 - C_3'}{C_0 - C_0'} \quad \text{(IVc)}$$

$$\frac{dC_0}{dC_0} = -K_7 \frac{C_3'}{C_0'} = K_4 \frac{C_4 - C_4'}{C_0 - C_0'} \quad \text{(IVd)}$$

wherein $K_1$, $K_2$ and $K_3$ are defined to be the ratios of diffusivities $D_m$: $K_1 = D_1/D_0$, $K_2 = D_2/D_0$, $K_3 = D_3/D_0$ and $K_4 = D_4/D_0$;

$C_m$ is the concentration of $AX_{4-n}Y_n$ in the bulk phase; and $C_m'$ is the concentration of $AX_{4-n}Y_n$ in the reaction film.

As before, $D_0$ corresponds to the diffusivity of $AX_4$, $D_1$ to the diffusivity of $AX_3Y$, $D_2$ to the diffusivity of $AX_2Y_2$, $D_3$ to the diffusivity of $AXY_3$ and $D_4$ to the diffusivity of $AY_4$. In the diffusional process reactant $AX_4$ is assumed to be the predominant constituent of the mass transfer film.

From these relationships expressions for the concentrations at the surface of the porous tube can be developed:

$$C_1' = \frac{(1/K_1) R C_0' + C_1}{1 + (K_5/K_1) R} \quad \text{(Va)}$$

$$C_2' = \frac{(K_5/K_7) R C_1' + C_2}{1 + (K_6/K_2) R} \quad \text{(Vb)}$$

$$C_3' = \frac{(K_6/K_3) R C_2' + C_3}{1 + (K_7/K_3) R} \quad \text{(Vc)}$$

$$C_4' = (K_7/K_4) R C_3' + C_4 \quad \text{(Vd)}$$

wherein $$R = C_0 - C_0'/C_0', \quad \text{(VI)}$$

and is therefore the ratio of (1) the difference between the bulk phase concentration and reaction film concentration of methane to (2) the reaction phase methane concentration.

Considering only the concentration $C_0$, it is evident that $$D_0(C_0 - C_0')/\Psi = k_0 C_0' \quad \text{(VII)}$$

wherein $\Psi$ is as defined above. Hence, $$R = k_0 \Psi / D_0. \quad \text{(VIII)}$$

Thus, R can be regarded as constant for any given reactor at a particular set of temperature, pressure and gas flow rate conditions.

A large value of R (e.g., $R > 3$) therefore implies that the reaction rate constant for $AX_4$ is large compared to the diffusion rate from the bulk phase into the reaction film. A large value of R can correspond to a large value of $k_0$ (reaction rate constant) and/or a large value of $\Psi$ (mass transfer film thickness) and/or a small value of $D_0$ (diffusivity). Under these circumstances the intermediate products formed will be further reacted to form predominantly $AY_4$ and thus lead to the suppression of the intermediate products which characterizes the porous tube reactor when operated in the laminar flow regime.

A small value of R (e.g., $R < 1$) implies that the diffusion rate for $AX_4$ is large compared to the reaction rate. For the limiting case in which $R = 0$, and hence in which the rate of diffusion is infinitely greater than the rate of reaction or the thickness of the mass transfer film is negligibly small, equations IVa to IVd reduce to those for the tubular flow reactor and the product composition from the porous tube reactor will be indistinguishable from that of the tubular flow reactor. One way of attaining a small value of R would be by inducing turbulence in the first elongated zone, e.g., in annular zone 15 in the porous tube reactor of FIG. 1, thus destroying the concentration difference between the surface of the porous tube and the bulk phase. This is equivalent to greatly increasing the value of $D_0$, the diffusivity of $AX_4$ or greatly decreasing the value of $\Psi$, the thickness of the mass transfer film.

Figure 7:
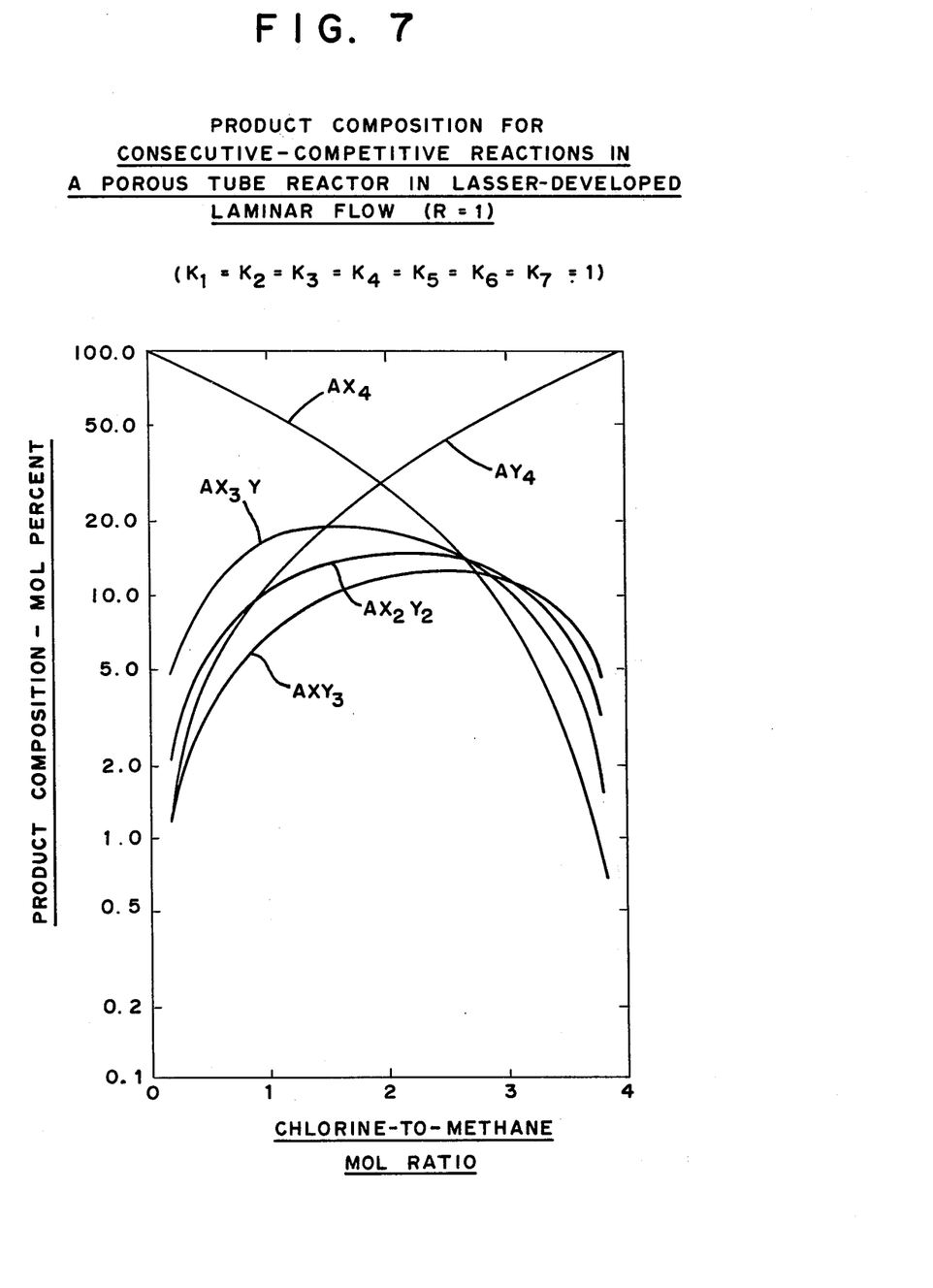
FIGS. 7, 8 and 9 are theoretical plots of product composition vs. chlorine-to-methane mol ratio for methane chlorination in a porous tube reactor with increasingly developed laminar flow (decreasing turbulence and bulk mixing).
Figure 8:
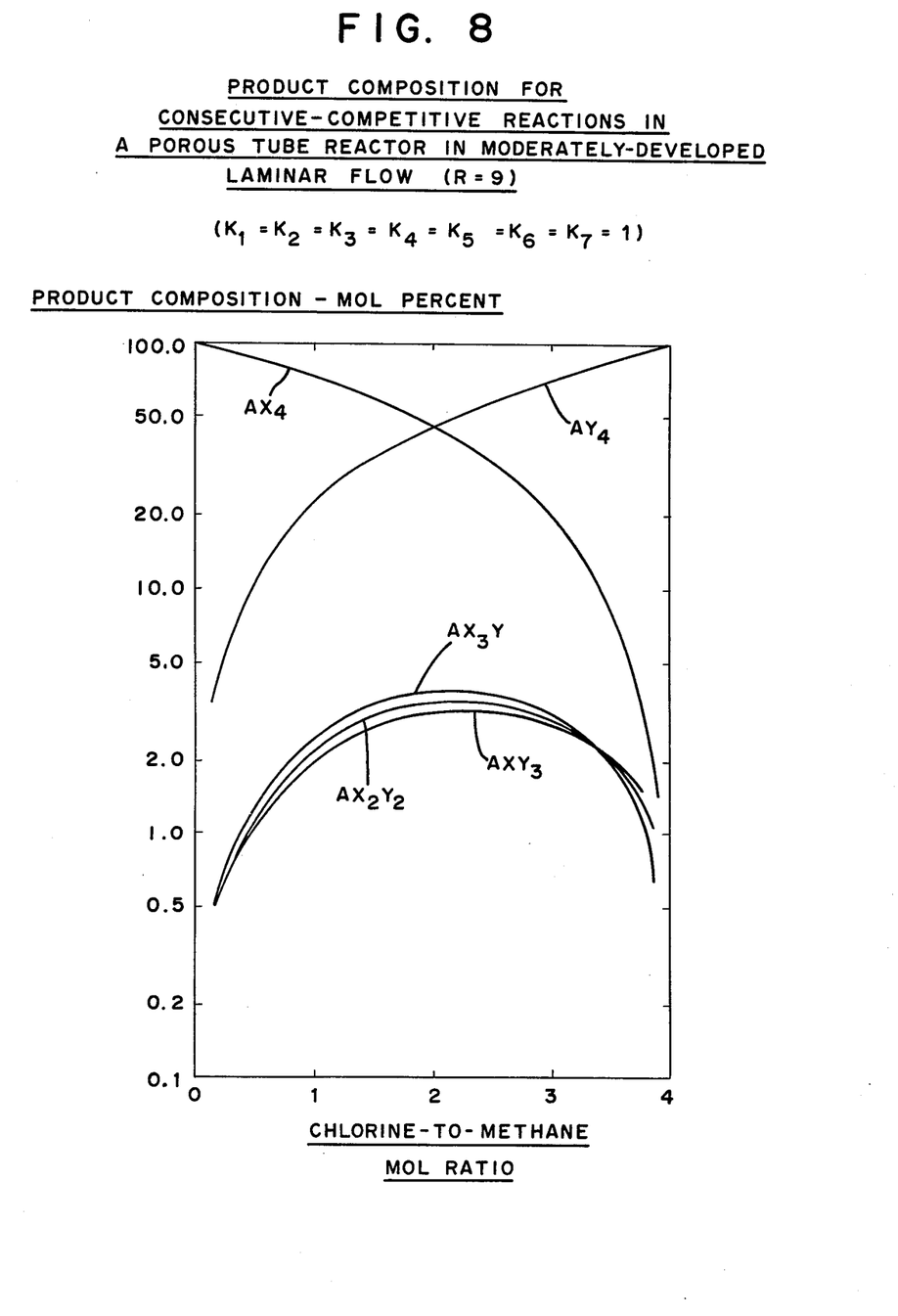
Figure 9:
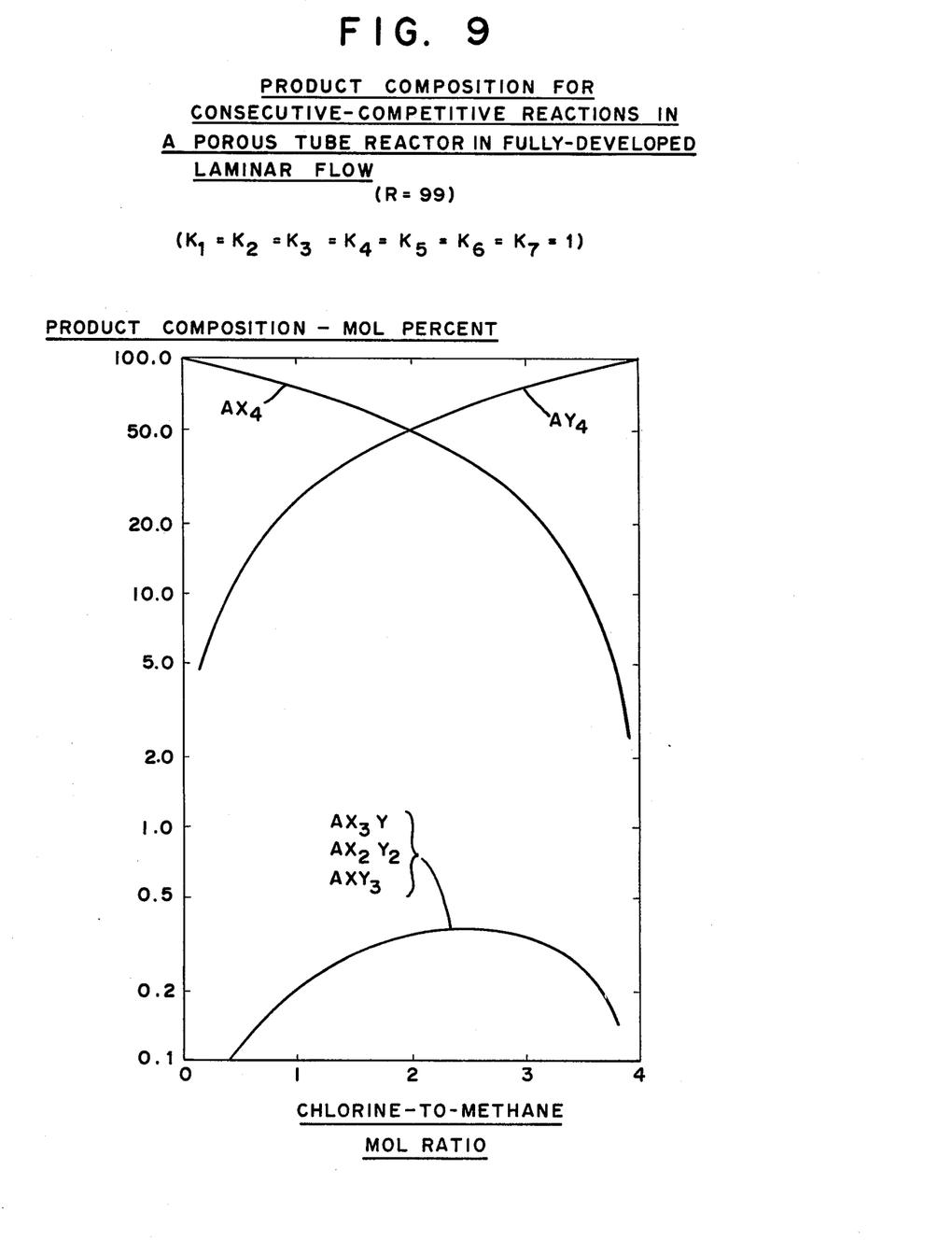
Figure 10:
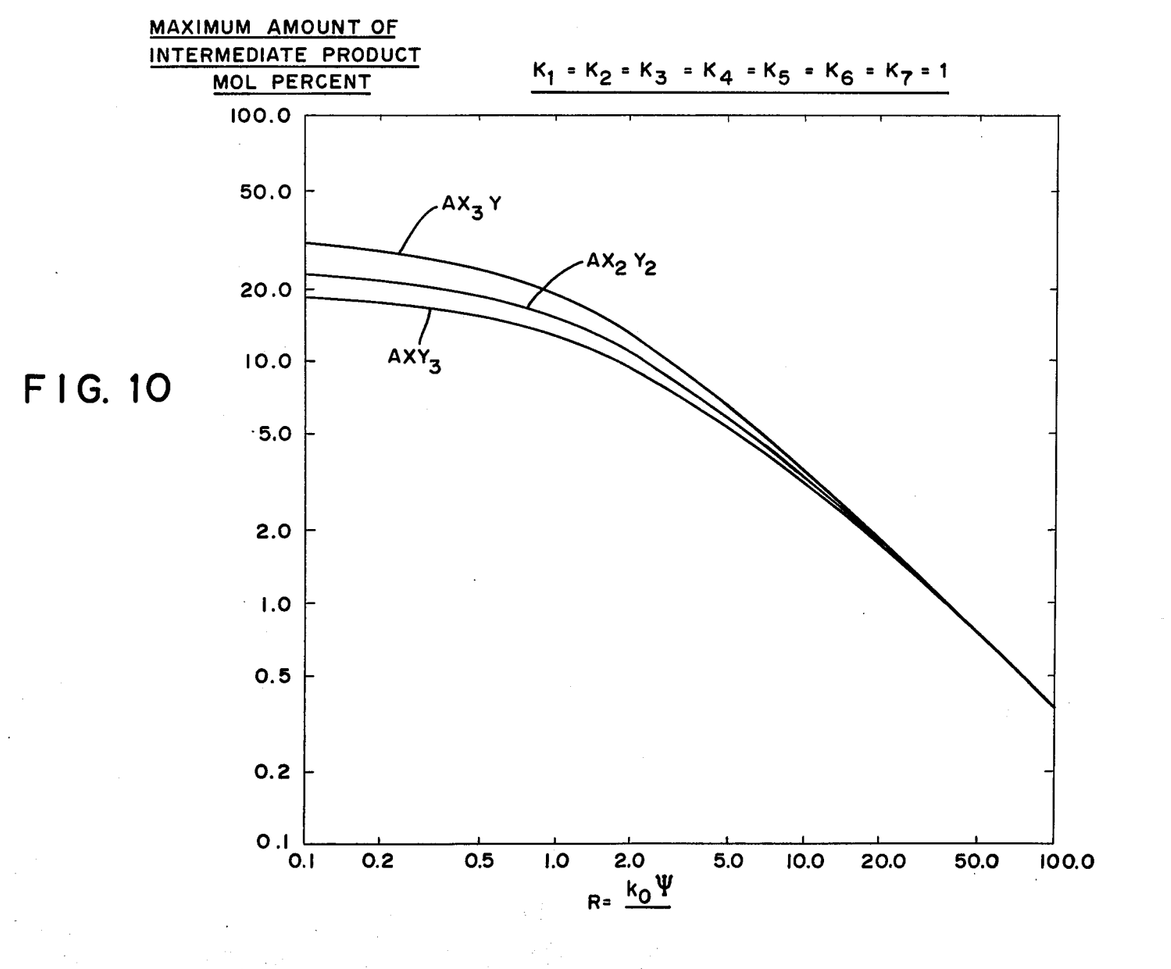
FIG. 10 is a plot of the effect of R-values (as defined below) on the maximum amount of intermediate partially chlorinated hydrocarbons for competitive-consecutive reactions using a porous tube reactor of FIG. 1.

FIGS. 7 through 9 show the product stream compositions calculated by numerical solution of the preceding equations IVa to IVd and Va to Vd for a feed consisting of pure $AX_4$, for values of R equal to 1, 9 and 99 in FIGS. 7-9, respectively. As R increases, it is evident that the concentrations of the intermediate products become progressively smaller. For example, the maximum concentration of $AX_3Y$ in an apparatus of the present invention using laminar flow through the first elongated gas zone (e.g., $R = 9$ for the porous tube reactor discussed above) is about one-tenth of the value obtained from a tubular flow reactor (i.e., wherein $R = 0$). The maximum concentration attained by each of the intermediate products as a function of R is shown by FIG. 10.

Thus, from this analysis, it can be seen that the apparatus of the present invention suppresses the formation of intermediate products of consecutive-competitive reactions when the flow of gas through the first elongated gas zone is in the laminar region and that the extent of this suppression depends on the value of R, which is a function of the reaction rate constant, diffusivity and mass transfer film thickness.

For the foregoing reasons, the process of the present invention is preferably characterized by an R of greater than about 1, more preferably at least about 5, in which R is as defined above in Equation VIII. While the above relationships (e.g., Equations IVa to VIII) were developed for porous tube reactors of the present invention, it should be understood that they are independent of geometry of the first and second elongated gas zones.

The chlorinated hydrocarbon produced in the apparatus in accordance with the present invention may be recovered from the gases exiting the reactor by conventional means, and a discussion of its recovery from these exit gases is not necessary here. Unreacted gas exiting the reactor may be recycled to the reactor for more complete chlorination where desired.

The process of the present invention may be further illustrated by reference to the following examples.

In the case of Examples 1–3, the reactor used comprises a porous tube of fritted Pyrex glass, having a pore size in the 0.9 to 1.4 micron range. It is 23.8 cm long, 4.3 cm O.D. and arranged concentrically within an outer tube 6.5 cm I.D. which is jacketed. Molten sodium nitrate is circulated through the jacket at a rate and temperature sufficient to maintain the reaction in an isothermal condition at the temperature specified. The chlorine is introduced into the porous inner tube, the methane or ethane into one end of the annulus. The products of reaction are removed from the other end of the annulus and pass through a condenser at −45° to −50° C. The non-condensibles leaving the condenser are principally unreacted ethane or methane plus hydrogen chloride. In all examples the flow rates and reactor dimensions were such that flow in the reaction zone (annulus) was well into the laminar regime. Reynold's numbers were in the range of 20 to 150. Product samples are analyzed in all examples by gas chromatography.

EXAMPLES 1 AND 2

These chlorinations are carried out with ethane as the raw material:

|  |  | Ex. 1 | Ex. 2 |
|---|---|---|---|
| Temperature |  | 360° C. | 360° C. |
| Chlorine flow (gram mols/sec) $\times 10^4$: |  | 1.2 | 2.4 |
| Ethane flow (gram mols/sec) $\times 10^4$ |  | 1.2 | 0.6 |
| Ratio of $Cl_2/CH_3CH_3$ |  | 1:1 | 4:1 |
| Pressure abs. of $Cl_2$ in porous tube |  | 31–32" Hg. | 31–32" Hg. |
| Pressure abs. of $CH_3CH_3$ in annulus |  | 30" Hg. | 30" Hg. |
| Composition in liquid product (mole %): |  |  |  |
| Vinyl Chloride | $CH_2:CHCl$ | 2.4 | 0.0 |
| Ethyl Chloride | $CH_3CH_2Cl$ | 7.4 | 0.1 |
| Vinylidene Chloride | $CH_2:CCl_2$ | 13.1 | 2.9 |
| Ethylidene Chloride | $CH_3CHCl_2$ | 10.4 | 1.5 |
| Trans-dichloroethylene | Tr . CHCl:CHCl | 3.6 | 3.0 |
| Cis-dichloroethylene | Cis -CHCl:CHCl | 6.3 | 4.5 |
| 1,2-Dichloroethane | $CH_2ClCH_2Cl$ | 0.5 | 1.3 |
| Methyl Chloroform | $CH_3CCl_3$ | 10.2 | 5.9 |
| Carbon Tetrachloride | $CH_3CCl_2$ | 1.1 | 0.5 |
| Trichloroethylene | $CHCl:CCl_2$ | 25.0 | 36.4 |
| Tetrachloroethylene | $CCl_2:CCl_2$ | 10.6 | 24.7 |
| 1,2,2,2-Tetrachloroethane | $CH_2ClCCl_3$ | 4.4 | 6.4 |
| Other |  | 6.1 | 13.3 |

Attention is called to the excellent yields of the desired products trichloroethylene and tetrachloroethylene. It is instructive to contrast these results with those obtained by chlorination of ethane in a conventional tubular flow reactor at comparable temperature and pressure and with the same chlorine to ethane ratio of 1:1 as for Example 1. According to McBee, et al., "Chlorination of Ethane", Industrial Engineering Chemistry, 41, No. 4, 799, at 802 (1949), the approximate composition of the liquid products would be (mol %):

| Vinyl Chloride ($CH_2:CHCl$) | 1 |
|---|---|
| Ethyl Chloride ($CH_3CH_2Cl$) | 75 |
| Ethylene Chloride ($CH_3CHCl_2$) | 17 |
| 1,2-Dichloroethane ($CH_2ClCH_2Cl$) | 7 |

Thus, while the conventional process leads predominantly to ethyl chloride and ethylidene chloride with negligible amounts of trichloroethylene and tetrachloroethylene, the process of this invention leads to much smaller amounts of ethyl chloride and ethylidene chloride and substantial amounts of trichloroethylene and tetrachloroethylene.

It is clear that this process using a porous tube reactor so designed as to operate under isothermal conditions, and controlled variables such as the degree of turbulence in the annular reaction zone, the temperature, the ratio of reactants, the feed rate and the pressure differential across the porous barrier, can provide effective control of the percentage composition of the chlorinated reaction products, thus the production of specific chlorinated products and groups of products in good yield can be obtained.

EXAMPLE 3

The conditions for this specific example in which methane is used as feed, are as follows:

| Temperature maintained | 350° C. |
|---|---|
| Chlorine flow (grams mols/sec) $\times 10^4$ | 1.4 |
| Methane flow (gram mols/sec) $\times 10^4$ | 1.4 |
| Ratio: $Cl_2/CH_4$ | 1:1 |
| Pressure abs. of $Cl_2$ in porous tube | 31–32" Hg. |
| Pressure abs. of $CH_4$ in annulus | 30" Hg. |
| Composition of liquid product (mole %): |  |
| Methyl chloride: ($CH_3Cl$) | 11.4 |
| Methylene chloride: ($CH_2Cl_2$) | 4.4 |
| Chloroform: ($CHCl_3$) | 6.3 |
| Carbon tetrachloride: ($CCl_4$) | 69.1 |
| Tetrachloroethylene: ($CCl_2:CCl_2$) | 17.6 |

The high yield of the desired carbon tetrachloride will be noted.

EXAMPLE 4

In the following Example, a different reactor was used which comprised a porous tube of sintered alumina, having an average pore size of 60 microns. The porous tube is 60 cm long, 1.9 cm O.D. and arranged concentrically within an outer tube 6.25 cm I.D. which is equipped with a heating/cooling means so as to maintain the reaction in an isothermal condition at the temperature specified. The chlorine is introduced into the porous inner tube and the methane into one end of the annulus. The products of reaction are removed from the other end of the annulus and pass through a condenser at −45° to −50° C. The non-condensibles leaving the condenser are principally unreacted methane plus hydrogen chloride.

The conditions for this specific example are:
Temperature maintained: 425° C.
Pressure abs. of $Cl_2$ in porous tube 31–32" Hg.
Pressure abs. of $CH_4$ in annulus: 30" Hg.

Several runs are made in which the $Cl_2/CH_4$ mole ratio in the feed is varied. These mole ratios and the composition of the product gas stream is set forth in Table I:

Table I

| Run No. | Cl$_2$/CH$_4$ Mole Ratio | Composition of Product Gas (Mole %) | | | |
|---|---|---|---|---|---|
| | | CH$_3$Cl | CH$_2$Cl$_2$ | CHCl$_3$ | CCl$_4$ |
| 1 | 0.67 | 5.0 | 18.1 | 29.1 | 47.6 |
| 2 | 1.74 | 4.1 | 16.5 | 31.3 | 47.4 |
| 3 | 2.14 | 4.0 | 12.4 | 26.0 | 55.8 |
| 4 | 2.76 | 2.2 | 5.3 | 13.4 | 70.1 |

The excellent yield of carbon tetrachloride and small quantity of by-products resulting from the use of the porous tube reactor may be compared with that obtained employing a conventional staged tubular flow reactor. Table II sets forth the tubular reactor data obtained by E. T. McBee, et al. in E. T. McBee, et al., "Chlorination of Methane", *Industrial and Engineering Chemistry*, 34, No. 3, 296, at 298 (1942), employed the Hass-McBee chlorination process referenced in that article.

Table II
Temperature: 440° C.

| Run No. | Cl$_2$/CH$_4$ Mole Ratio | Composition of Product Gas (Mole %) | | | |
|---|---|---|---|---|---|
| | | CH$_3$Cl | CH$_2$Cl$_2$ | CHCl$_3$ | CCl$_4$ |
| 1 | 0.50 | 62.0 | 30.0 | 7.0 | 1.0 |
| 2 | 1.10 | 37.4 | 41.0 | 18.9 | 2.6 |
| 3 | 1.68 | 19.0 | 43.1 | 33.4 | 4.4 |
| 4 | 1.98 | 10.7 | 34.8 | 45.5 | 9.1 |
| 5 | 2.28 | 5.3 | 29.2 | 51.7 | 13.7 |
| 6 | 3.02 | 2.7 | 15.1 | 52.9 | 29.2 |
| 7 | 3.31 | — | 5.7 | 43.5 | 50.9 |
| 8 | 3.88 | — | — | 4.0 | 96.0 |

Thus, whereas use of a Cl$_2$/CH$_4$ mole ratio of 3.02 (Run 6) in the staged tubular flow reactor produced a product gas containing only 29.2 mole percent CCl$_4$, the porous tube reactor, employing a Cl$_2$/CH$_4$ mole ratio 8.6 percent *lower* (i.e., 2.76 mole ratio, Run 4), achieved a product gas containing 70.1 mole percent CCl$_4$, for greater than a 58 percent improvement in the carbon tetrachloride content in the gas product. Moreover, these greatly improved yields, and concomitant decreased by-products, are obtained using a lower temperature of reaction (425° vs. 440° C.).

EXAMPLE 5

Employing the porous tube reactor of Example 4, the following chlorinations are carried out with methyl chloride as the raw material, using the method of handling the reactants and products as employed with methane fed in Example 4:

Temperature: 425° C.
Pressure abs. of Cl$_2$ in porous tube: 31–32"Hg.
Pressure abs. of CH$_3$Cl in porous tube 30"Hg.

As in Example 4, several runs are made in which the Cl$_2$/CH$_3$Cl mole ratio in the feeds are varied. The mole ratios employed and the composition of the product gases obtained are set forth in Table III.

TABLE III

| Run No. | Cl$_2$/CH$_3$Cl Mole Ratio | Composition of Product Gas (Mole %) | | |
|---|---|---|---|---|
| | | CH$_2$Cl$_2$ | CHCl$_3$ | CCl$_4$ |
| 1 | 0.67 | 49.9 | 27.7 | 22.2 |
| 2 | 1.74 | 26.6 | 32.5 | 39.4 |
| 3 | 2.14 | 11.1 | 20.9 | 64.4 |

The excellent CCl$_4$ yields and low by-product formation obtained using the porous tube reactor may be seen by reference to the data summarized in Table IV, which relates methyl chloride chlorination employing a staged tubular flow reactor as described in Bruce E. Kurtz, "Homogeneous Kinetics of Methyl Chloride Chlorination", *Industrial Engineering Chemical Process Design and Development*, Vol. 11, No. 3, 332, at 336 (1972).

Table IV
Temperature: 460° C.

| Run No. | Cl$_2$/CH$_3$Cl Mole Ratio | Composition of Product Gas (Mole %) | | |
|---|---|---|---|---|
| | | CH$_2$Cl$_2$ | CHCl$_3$ | CCl$_4$ |
| 1 | 0.5 | 77.5 | 20.0 | 2.5 |
| 2 | 1.0 | 62.1 | 33.3 | 4.5 |
| 3 | 1.5 | 36.2 | 46.8 | 16.4 |
| 4 | 2.0 | 21.0 | 47.4 | 31.6 |
| 5 | 2.5 | 4.0 | 38.4 | 57.6 |

Thus, the porous tube reactor produced a gas containing 64.4 mole percent CCl$_4$ using a Cl$_2$/CH$_3$Cl mole ratio of only 2.14 (Run 3), whereas the 14 percent higher Cl$_2$/CH$_3$Cl mole ratio of 2.5 (Run 5) using the staged tubular flow reactor yielded a product gas containing only 57.6 mole percent CCl$_4$, which is over 10% less CCl$_4$ in the product.

In the above examples it is possible to determine values of R by inserting into Equations IVa to IVd and Va to Vd the actual values, known to those skilled in the art by reference to the published literature or by experimental determination by published techniques, for the reaction rate constant ratios (K$_5$ through K$_7$) and the diffusivity ratios (K$_1$ through K$_4$) and calculating product composition curves of the type shown by FIGS. 7 to 9 by standard mathematical techniques, also known to those skilled in the art, for various values of R. The correct value of R is that value which corresponds to the product composition at a given chlorine-to-methane mol ratio which best agrees with the actual product composition obtained experimentally at the same chlorine-to-methane mol ratio. For example, employing the method described above to the results of Example 3 it is found that an R value of 9 gives a product composition which best agrees with the actual product composition of Example 3. Values of R corresponding to the results of the other examples can be calculated in the same fashion and will be found to be in the approximate range of 1 to 10.

Other modes of applying the principle of the invention may be employed instead of those explained, change being made as regards the method or compounds herein disclosed, provided the steps or compounds stated by any of the following claims, or the equivalent of said stated steps or compounds, be employed.

I claim:

1. A process for isothermal chlorination of a feed stream selected from the group consisting of hydrocarbons having from 1 to 2 carbon atoms, their partially chlorinated derivatives and mixtures thereof, to form chlorinated hydrocarbons under improved temperature and distribution conditions which comprises: (a) passing said feed stream under pressure and in laminar flow into one end of a first elongated gas zone, (b) passing a gas containing chlorine into a second elongated gas zone positioned along said first gas zone, said first and second elongated gas zones being separated along the major length thereof by a porous member, (c) maintaining the pressure of the gas in said second gas zone in excess of the pressure in said first gas zone for diffusion of chlorine into said first gas zone, (d) maintaining said first gas zone under conditions sufficient to effect reaction therein of at least a portion of said diffused chlorine with the feed stream for production of the desired chlorinated hydrocarbon, and (e) withdrawing the gas product containing the desired chlorinated hydrocarbon from the other end of said first gas zone.

2. The process of claim 1 wherein the temperature within the first elongated zone is maintained within the range of from about 250°–500° C.

3. The process of claim 1 wherein the molar ratio between the chlorine and the hydrocarbon in the first elongated zone is from about 0.5:1 to 5:1.

4. The process of claim 1 wherein the first elongated gas zone is substantially annular, and said second elongated gas zone is disposed internally in said porous member, said member comprising a porous tube closed at one end and positioned at the core of said annular first gas zone.

5. The process of claim 4 wherein the first gas zone is characterized by a length-to-diameter ratio of at least about 3:1.

6. A process for chlorinating a feed stream selected from the group consisting of methane, partially chlorinated methane derivatives and mixtures thereof, under improved temperature and distribution conditions, to form carbon tetrachloride, which comprises: passing chlorine through a feed inlet to a first elongated zone surrounded by a porous member through which the chlorine diffuses; introducing the hydrocarbon feed into a second elongated reaction zone surrounding the porous member; regulating the rate of flow of gas through said gas zones at a rate such that laminar flow is maintained in the second elongated reaction zone; and discharging the gas product containing carbon tetrachloride from the second elongated reaction zone at a point remote from the feed inlet.

7. The process of claim 1 wherein the porous member is characterized by an average pore size of from greater than about 0.5 up to about 1000 microns.

* * * * *